US011738103B1

(12) United States Patent
Jabat Rico et al.

(10) Patent No.: US 11,738,103 B1
(45) Date of Patent: Aug. 29, 2023

(54) NEBULIZER DEVICE

(71) Applicant: LAINOMEDICAL S.L., Gipuzkoa (ES)

(72) Inventors: Gonzalo Jabat Rico, Gipuzkoa (ES); Francesc Paris Huguet, Gipuzkoa (ES)

(73) Assignee: LAINOMEDICAL S.L., Gipuzkoa (ES)

( * ) Notice: Subject to any disclaimer, the term of this patent is extended or adjusted under 35 U.S.C. 154(b) by 0 days.

(21) Appl. No.: 17/731,876

(22) Filed: Apr. 28, 2022

(30) Foreign Application Priority Data

Mar. 28, 2022 (EP) .................................... 22382288

(51) Int. Cl.
| | |
|---|---|
| *A61M 1/06* | (2006.01) |
| *A61L 2/10* | (2006.01) |
| *A61M 11/00* | (2006.01) |
| A61M 31/00 | (2006.01) |
| A61M 37/00 | (2006.01) |
| A61M 1/00 | (2006.01) |
| A61M 5/00 | (2006.01) |
| A61M 5/178 | (2006.01) |
| A61M 25/00 | (2006.01) |
| A61C 17/00 | (2006.01) |

(52) U.S. Cl.
CPC .............. *A61L 2/10* (2013.01); *A61M 11/005* (2013.01); *A61L 2202/11* (2013.01); *A61L 2202/24* (2013.01); *A61M 2205/8206* (2013.01); *A61M 2205/8237* (2013.01)

(58) Field of Classification Search
CPC ........ A61M 1/06; A61M 31/00; A61M 37/00; A61M 1/00; A61M 5/00; A61M 5/178; A61M 25/00; A61M 35/003; A61C 17/00; A61C 1/16; A61C 15/00; A45D 2034/005; A45D 2200/155
See application file for complete search history.

(56) References Cited

U.S. PATENT DOCUMENTS 5,707,715 A * 1/1998 deRochemont ...... H05K 1/0271
428/209
2010/0222752 A1 9/2010 Collins, Jr. et al.

FOREIGN PATENT DOCUMENTS

| DE | 202011004834 U1 | 6/2011 |
|---|---|---|
| JP | 5823864 B2 * | 10/2009 |
| KR | 20090087605 A | 8/2009 |
| WO | 2016028525 A1 | 2/2016 |

(Continued)

*Primary Examiner* — Erich G Herbermann
*Assistant Examiner* — Ilya Y Treyger
(74) *Attorney, Agent, or Firm* — Edell, Shapiro & Finnan, LLC (57) ABSTRACT

The present disclosure relates to a device for nebulizing a liquid composition and to methods for disinfecting an internal channel of the nebulizer device. The device includes a channel connecting a liquid composition inlet, a mesh and a liquid composition outlet. The mesh divides the channel into an input channel portion and into an output channel portion. The channel is at least partially optically transparent to bacterial disinfecting electromagnetic radiation. The device (56) References Cited

FOREIGN PATENT DOCUMENTS

| WO | 2016087752 | A1 | 6/2016 |
| WO | 2016162395 | A1 | 10/2016 |
| WO | 2016205537 | A1 | 12/2016 |
| WO | 2021014314 | A1 | 1/2021 |

* cited by examiner

NEBULIZER DEVICE

CROSS-REFERENCE TO RELATED APPLICATIONS

This application relates to and claims the benefit and priority to European Application No. EP22382288.3, filed Mar. 28, 2022.

FIELD

The present disclosure relates to devices for nebulizing a liquid composition. More specifically, the present disclosure relates to nebulizer devices comprising a disinfection system. The present disclosure also relates to methods for disinfecting the nebulizer device.

BACKGROUND

Nebulizer devices allow gaseous administration of medical as well as non-medical products. Nebulizers are used, among others, in the medical field of aerosol therapy. They are generally used to treat numerous diseases, for example diseases affecting the respiratory system. The nebulization, or atomization, of a liquid composition allows to disperse the liquid composition into a plurality of fine droplets having diameters in the range of micrometers. These droplets are easily inhaled by the user of the nebulizer, reaching most of the respiratory system.

There are many types of nebulizer devices known in the art, such as conventional jet nebulizers, which use compressed air or oxygen to break up a thin film or jet of fluid into droplets suitable for inhalation; or ultrasonic nebulizers, which for example use the high frequency vibrations of a piezoelectric element submerged in the liquid product for generating droplets which a forced air flow expels. Other types of ultrasonic nebulizers comprise a very thin membrane or mesh provided with a plurality of micrometric holes. The mesh is coupled to a piezoelectric element that vibrates at high frequency. The vibrations are transmitted to the mesh, which produces a very fine nebulization of the liquid product, dispensing it to the user of the nebulizer.

Modern nebulizers are generally designed as portable devices, which should be easy and quick to use in a broad range of conditions. Almost all nebulizers on the market today require the user to obtain a container (a vial, a bottle or similar) and pour the liquid product into a reservoir in the nebulizer. This may lead to undesired liquid spills outside the dedicated opening of the nebulizer, resulting in poor cleanliness of the nebulizer. Other known nebulizers are configured to receive a vessel containing a liquid product. In both cases, the nebulizer should be cleaned periodically for avoiding contamination and undesired growth of organisms in it.

Cleaning an inside of the nebulizer, for example a channel which directs the liquid product to a user receiving the nebulized product, may be challenging. Direct accessibility to the inner surfaces to be cleaned may be difficult or impossible. Also, common products and techniques available in a household may not be suitable for cleaning an inside of the nebulizer. For example, introducing potable water inside the nebulizer may damage or deteriorate the nebulizer, e.g. a mesh to be vibrated. Inadequate drying may also contribute to the development of bacteria. When a user is out of home, cleaning the nebulizer may also not be easy.

The present disclosure aims at improving disinfection of a nebulizer device.

SUMMARY

According to a first aspect of the disclosure, a device for nebulizing a liquid composition is provided. The device comprises a channel connecting a liquid composition inlet for receiving a liquid composition, a mesh configured to be vibrated by a mesh actuator for nebulizing the liquid composition to be nebulized, and a liquid composition outlet for expelling a nebulized liquid composition. The mesh divides the channel in an input portion of the channel and an output portion of the channel. The channel is at least partially optically transparent to disinfecting radiation. The device further comprises a first emitter arranged at a first side of the mesh configured to illuminate the input portion of the channel with disinfecting electromagnetic radiation. The device further comprises a second emitter arranged at a second opposite side of the mesh configured to illuminate the output portion of the channel with disinfecting electromagnetic radiation.

According to this aspect, disinfecting electromagnetic radiation can clean and disinfect the channel of the nebulizer device, in particular an inside surface of the channel, in an effective manner. Both the channel portion for guiding a liquid composition to the mesh and the channel portion for guiding a nebulized composition away of the mesh can be disinfected. The mesh can also be disinfected. Risk of damage or deterioration of one or more components of the nebulizer device, e.g. of the mesh, may be reduced in comparison with the use of cleaning liquids.

As a liquid is not used for cleaning, it does not remain inside the channel and a risk of bacteria growth may be further reduced. Also, cleaning products separate from the nebulizer device are not required. The nebulizer device may therefore be disinfected in any place. Disinfection is also simplified for the users, who do not have to handle any particular cleaning product.

Disinfecting electromagnetic radiation may be bacterial disinfecting radiation, and may relate specifically to ultraviolet (UV) radiation. The disinfecting electromagnetic radiation may also relate to blue light having a wavelength in the range of 380-495 nanometers.

Ultraviolet radiation may be understood as the portion of the electromagnetic spectrum between X-rays and visible light. Ultraviolet radiation is usually divided in three regions or bands: the UVA region having wavelengths between 316 and 400 nm, the UVB region having wavelengths between 281 and 315 nm, and the UVC region having wavelengths between 100 and 280 nm. The UVC band is the more energetic band, and UVC radiation may effectively kill microorganisms. The first and second emitters may emit ultraviolet radiation in this band.

The term “liquid composition” is herein used to describe both liquids containing medically active ingredients in therapeutically effective amounts, and liquids which do not contain medically active ingredients, such as e.g. salted water, physiological serums and others. The expression “therapeutically effective amount” as used herein refers to an amount of a nebulized liquid composition which is sufficient to treat disease to which it is addressed. The specific dose of the liquid composition or active ingredient to obtain a therapeutic benefit may vary depending on the particular circumstances of the case.

In a further aspect, a method for disinfecting the channel of a nebulizer is provided. The method comprises initiating the channel disinfection. The method further comprises illuminating an input portion of the channel with disinfecting electromagnetic radiation from a first emitter arranged at a first side of a mesh of the nebulizer, and illuminating an output portion of the channel with disinfecting electromagnetic radiation from a second emitter arranged at a second opposite side of the mesh. The method further comprises ending the channel disinfection.

According to this second aspect, the method allows a user to disinfect the channel of the nebulizer effectively, easily and safely without carrying any cleaning product and in any place.

BRIEF DESCRIPTION OF THE DRAWINGS

Non-limiting examples of the present disclosure will be described in the following, with reference to the appended drawings, in which.

DETAILED DESCRIPTION

Reference now will be made in detail to embodiments of the present disclosure, one or more examples of which are illustrated in the drawings. Each example is provided by way of explanation only, not as a limitation. In fact, it will be apparent to those skilled in the art that various modifications and variations can be made in the present disclosure. For instance, features illustrated or described as part of one embodiment can be used with another embodiment to yield a still further embodiment. Thus, it is intended that the present disclosure covers such modifications and variations.

Figure 1A:
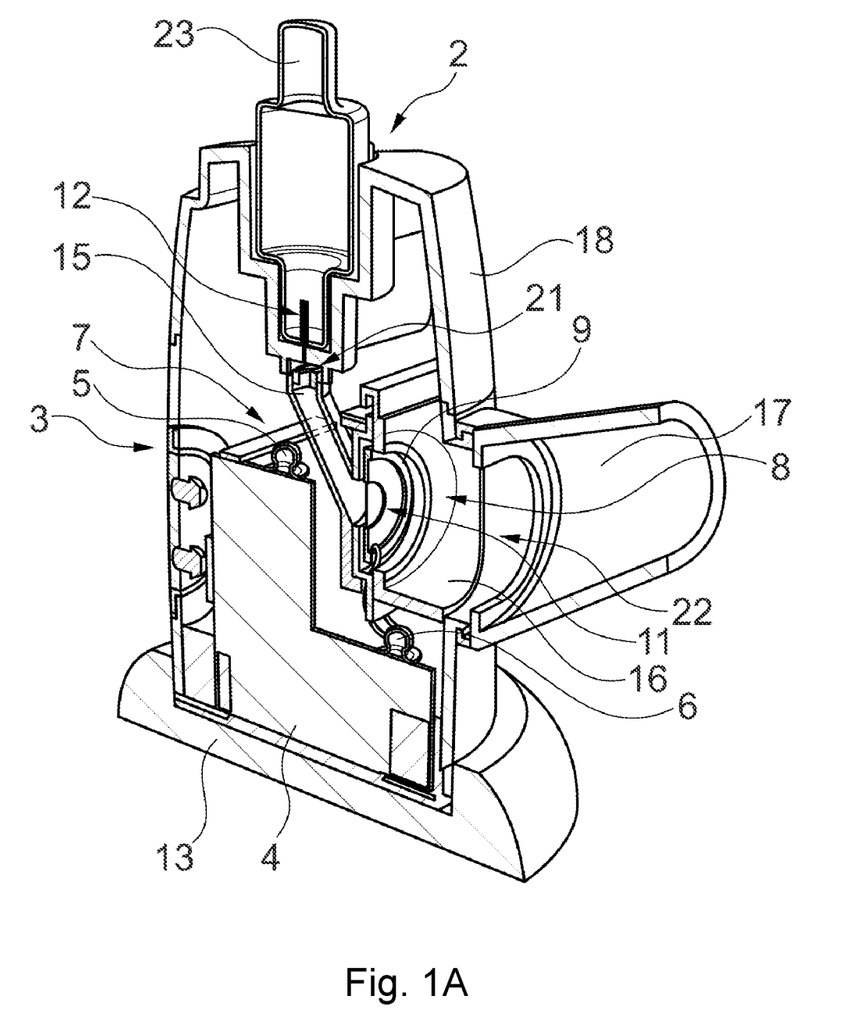
FIG. 1A illustrates a perspective view of an inside of a nebulizer device according to an example.
Figure 1B:
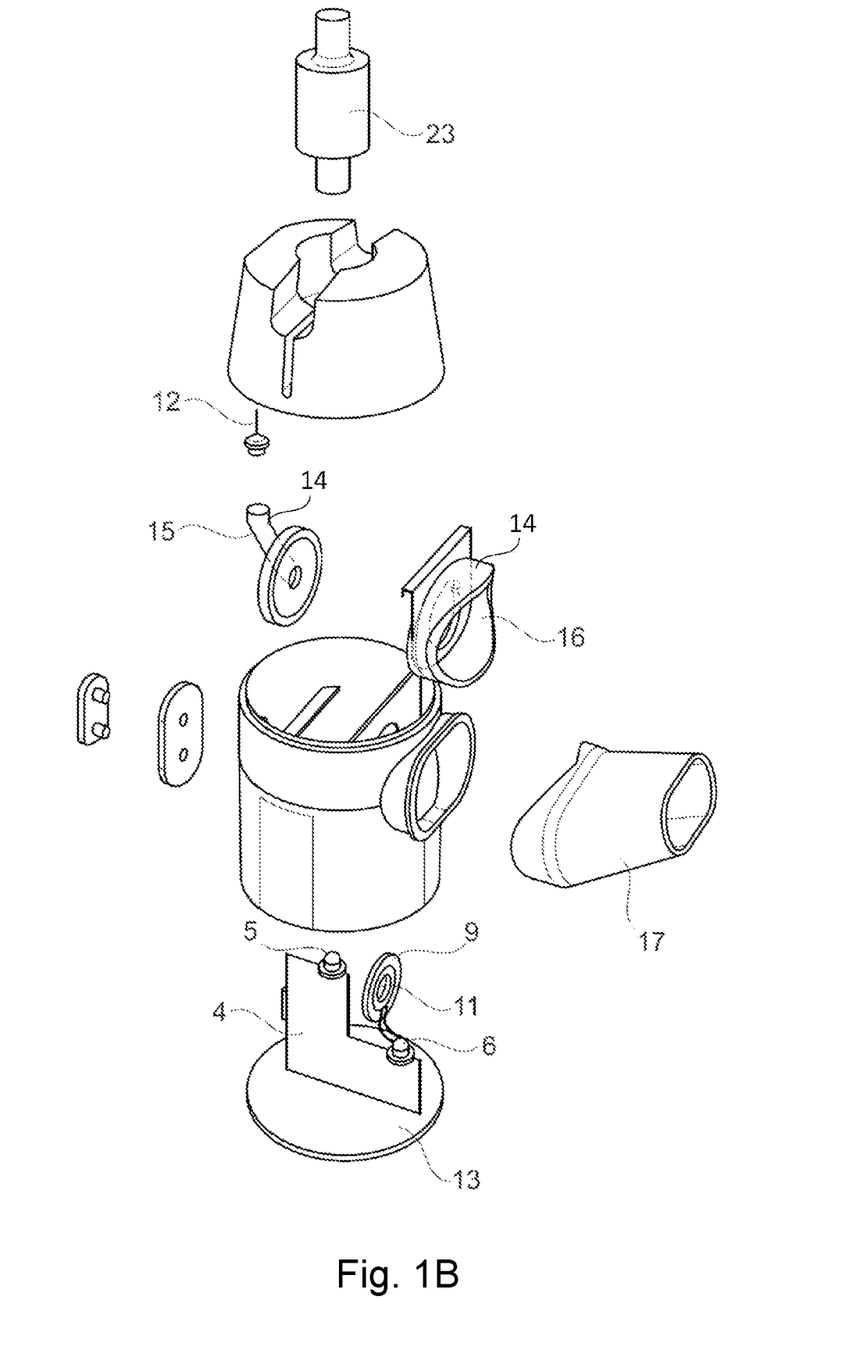
FIG. 1B illustrates an exploded view of the nebulizer device of the example of FIG. 1A.
Figure 2:
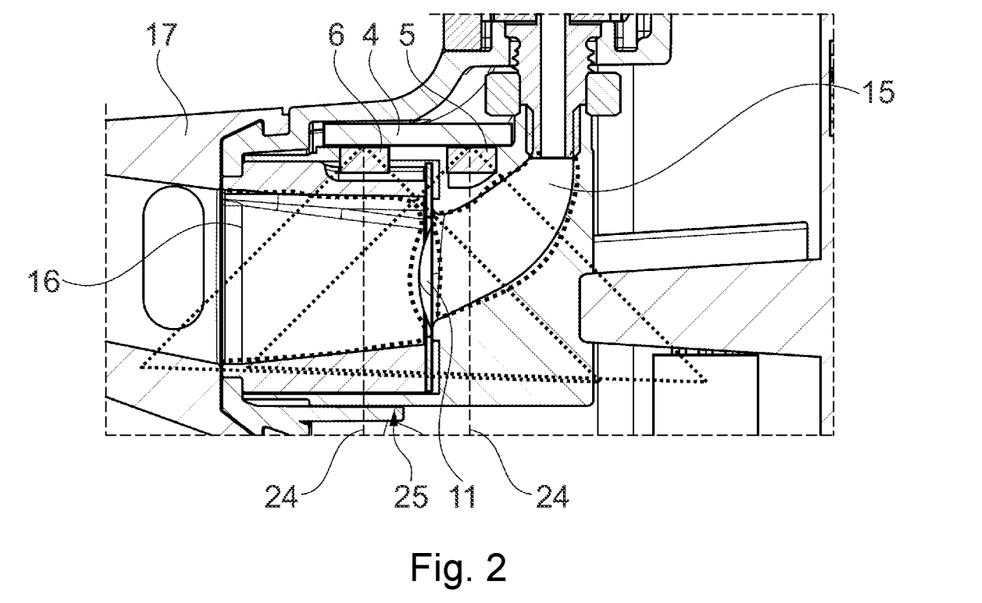
FIG. 2 illustrates a cross-sectional view of an inside of a nebulizer device according to another example.

FIG. 1A illustrates a perspective view of an inside of a nebulizer device according to an example of the present disclosure. FIG. 1B illustrates an exploded view of the nebulizer of FIG. 1A. FIG. 2 illustrates a cross-sectional view of a portion of an inside of a nebulizer device according to another example of the present disclosure. Various aspects of the present disclosure will be commented with respect to these examples.

The nebulizer device 10 for nebulizing a liquid composition comprises a liquid composition inlet 21 for receiving a liquid composition to be nebulized and a liquid composition outlet 22 for expelling the nebulized liquid composition. The nebulizer device 10 further comprises a mesh 11 and a mesh actuator 9 configured to vibrate the mesh 11 to nebulize the liquid composition. The nebulizer device 10 further comprises a channel 14 connecting the liquid composition inlet 21, the mesh 11, and the liquid composition outlet 22.

Therefore, a liquid composition can be introduced into the channel 14, in particular into an input portion of the channel 15, through the liquid composition inlet 21. The liquid composition is then guided to the mesh 11, which nebulizes it when the mesh actuator 9 causes the mesh 11 to vibrate, and the liquid composition is then expelled through an output portion of the channel 16. In some examples, the mesh actuator 9 may be a piezoelectric element circumferentially surrounding the mesh 11. In other examples, other actuators to set the mesh in rotation may be used.

The mesh 11 and mesh actuator 9 therefore divide the channel 14 into the input portion 15, through which the liquid composition travels and arrives at the mesh 11, and the output portion 16, through which the liquid composition already nebulized is expelled.

The nebulizer device 10 further comprises a first emitter 5 arranged at a first side of the mesh 7 which is configured to illuminate the input portion of the channel 15. The nebulizer device 10 further comprises a second emitter 6 arranged at a second opposite side of the mesh 8 which is configured to illuminate the output portion of the channel 16. The first side 7 and the second side 8 of the mesh 11 refer to axial sides of the mesh 11. I.e., the first and second emitters are spaced apart at least in a horizontal direction. The horizontal direction may be parallel to a bottom cover 13 of the nebulizer device 10. For example, the first emitter 5 may be below the input portion of the channel 15 and the second emitter 6 may be below the output portion of the channel 16.

The first and second emitters 5,6 are each configured for emitting (bacterial) disinfecting electromagnetic radiation. In this example, first and second emitters 5,6 may be UVC emitters. In other examples, emitters of other disinfecting light may be used. Although in the following reference is made specifically to UV or UVC radiation, other electromagnetic radiation suitable for disinfecting may also be used as mentioned before.

The channel 14 in this example is at least partially optically transparent to ultraviolet, UV, radiation. The channel 14 may be totally optically transparent to UV radiation.

A separation between the first 5 and second 6 UVC emitters, e.g. in a horizontal direction, may be such that a conduit region 25 between the UVC emitters is irradiated at least by one of the UVC emitters. The location of the UVC emitters may therefore depend on the opening angle of the emitters.

In the example of FIG. 2, the first 5 and second 6 UVC emitters are separated such that a conduit region 25 between the UVC emitters is irradiated by both the first 5 and second 6 UVC emitters. In particular, the mesh 11 and the surroundings of the mesh 11 are irradiated by both UVC emitters. A separation between the UVC emitters may in general be measured as the shortest distance between them, it does not need to be in a horizontal direction.

In some examples, the first 5 and second 6 UVC emitters may emit UVC radiation having a wavelength between 260 and 270 nm, e.g. between 262 and 266 nm. This wavelength range within the UVC band may be particularly effective for killing *E. coli*.

The input 15 and output 16 channel portions may be separate pieces in some examples, see e.g. FIG. 1B. In other examples, a channel 14 may be integrally formed.

In some examples, the nebulizer device 10 may comprise a nozzle 17. The nozzle 17 may be integrally formed with a casing 18 of the nebulizer device 10 in some examples. A nozzle 17 may help to guide and deliver the nebulized liquid composition to a user. The output portion 16 of the channel 14 may end where the nozzle 17 begins. The nozzle 17 may be provided as an independent component from the casing 18 in other examples. A removable nozzle 17 may be easier to clean. The nozzle 17 may be coupled to the nebulizer device 10 using different fastening mechanisms. In some examples, the coupling may be a threaded coupling. Alternatively, the coupling between the nozzle 16 and the device 10 may be performed using other types of connectors such as pressure fittings or others. The nozzle 17 may be a disposable nozzle or a re-usable nozzle. In some examples, the nozzle may connect with a mask which may be attached to a patient's head, e.g. to a child's head. A nebulized composition may therefore be delivered to the child's through the nozzle and the mask.

The device may further comprise a UVC emitter actuator 3 configured to activate, e.g. to switch on, the first 5 and second 6 UVC emitters in some examples. The UVC emitter actuator 3 may be a button which, when pressed, causes the UVC emitters to emit UVC light, thereby illuminating the first 15 and second 16 portions of the channel 14. The UVC emitter button 3 may be located in the casing 18. The UVC emitter button 3 may be linked with a mechanical switch or an electronic switch configured to initiate the disinfection.

In other examples, the nebulizer device 10 may be configured to activate the first 5 and second 6 UVC emitters during charging, and specifically upon detection of the charging of the nebulizer device. When the device 10 starts to be charged, a sensor may detect it and the device may activate the first 5 and second 6 UVC emitters in reply. As a battery of the nebulizer device 10 for causing the mesh actuator 9, and therefore the mesh 11, to vibrate, may need to be charged, the channel 14 of the nebulizer device 10 may always be disinfected if the nebulizer device 10 is configured to start disinfection with the charging of the battery of the nebulizer device. This may be convenient for the user, as remembering to specifically disinfect the channel 14 would not be required. It would also be ensured that the channel 14 is maintained disinfected and in good conditions for users who may find difficult to remember to manually activate the disinfection or to be consistent with the disinfection over time, e.g. children or elderly people. Moreover, the overall battery capacity may be reduced.

The first 5 and second 6 UVC emitters may be attached to the same (single) electronics carrier, e.g. the same printed circuit board, PCB, 4. The PCB 4 in this example may comprise the necessary circuit connections to control and activate and deactivate the light emitting diodes (LEDs) and the piezoelectric for vibrating the mesh for nebulizing. Assembly of the nebulizer device is facilitated and good and reliable control of the UVC emitters, both electrically and mechanically, may be obtained in an easy and simple manner. In other examples, multiple electronics carriers may be used, e.g. one per UVC emitter, or a dedicated PCB 4 for the LEDs.

In some examples, the PCB 4 may have a metallic outer layer configured to dissipate heat, e.g. having a thermal conductivity over 200 W/m·K. The metallic outer layer may be provided at a front side of the PCB. A front side of the PCB may refer to the side to which the UVC emitters 5, 6 are attached if surface-mount technology is used to attach them, or to the component side if through-hole technology is used to attach them. In other examples, the metallic outer layer may be provided at a back side of the PCB. The back side of the PCB is the side opposite the front side. In other examples, both a front and a back metallic outer layer may be provided. Using UVC radiation may heat an outer surface of the PCB. Providing a metallic outer layer may facilitate heat dissipation away from the UVC emitters in a compact manner.

A metallic outer layer may comprise metals such as aluminium, copper, or others. A metal, e.g. aluminium or copper, may refer both to the chemical elements, e.g. aluminium and copper, as well as to corresponding metal alloys. Aluminium alloys, e.g. aluminium and copper alloys. Aluminium alloys having a thermal conductivity between 200 and 230 W/m·K, or copper alloys having a thermal conductivity between 380 and 410 W/m·K, may be used in some examples.

Still in other examples, the PCB 4 may be entirely made of a metal e.g. having a thermal conductivity over 200 W/m·K. Heat dissipation may be further enhanced in this way. The PCB may for instance be made of aluminium, e.g. the chemical element aluminium.

In addition, or as an alternative to a metallic PCB or a coated PCB, the UVC emitters 5, 6 may be partially covered by a heat sink compound. A suitable heat sink compound, also known as heat sink paste, may be applied to the UVC emitters for increasing heat dissipation. Coverage by a heat sink compound is only partial, as a total coverage would blocking the passage of UVC radiation.

Using one or more of the abovementioned ways for dissipating heat away from the UVC emitters 5, 6 may help to keep their temperature below 90° C., e.g. below 70° C. or below 50° C. in some examples, and therefore to avoid a fast deterioration of the UVC emitters and surrounding elements.

The PCB 4 may be attached to a bottom cover 13 of the nebulizer device 10 in some examples, see FIGS. 1A and 1B. Stability of the PCB 4 and the first 5 and second 6 UVC emitters may be increased. The PCB 4 may be attached to the bottom cover 18 though an adhesive in some examples. In these or other examples, one or more recesses configured to receive the PCB may be provided. Some PCB retainers, e.g. recesses, slits or others, may additionally be provided in an inside of a lateral cover of the nebulizer device. Accurate positioning of the PCB as well as of the first and second UVC emitters may be achieved.

In some examples, the PCB 4 may be substantially perpendicular to the bottom cover 13 of the nebulizer device 10. For instance, if the bottom cover 13 extends horizontally, the PCB 4 may extend vertically. Arranging the first 5 and second 6 UVC emitters at a desired position may be easier with a vertical PCB e.g. if the PCB is attached to the bottom cover 13. In some examples, the UVC emitters 5, 6 may protrude beyond the PCB 4 towards the channel 4, e.g. vertically.

The PCB 4 carrying the first 5 and second 6 UVC emitters may be a dedicated PCB in other examples, see FIG. 2. In the example of this figure, a PCB 4 separate from other PCBs or electronics carriers, e.g. from a main PCB or a main electronics carrier of the nebulizer device 10 is provided. Distances between the UVC emitters and the channel 14, as well as a separation between the UVC emitters, may be better adjusted by arranging the UVC emitters on a dedicated PCB 4. A better usage of the space available inside the nebulizer device 10 may also be achieved in this way.

In some examples, irrespective whether the UVC emitters are arranged on a dedicated or non-dedicated PCB 4, the first 5 and second 6 UVC emitters may be arranged at different heights with respect to the bottom cover 13. A distance between each channel portion 15, 16 and the corresponding UVC emitter 5, 6 may therefore be adapted to the channel portion to be illuminated. The PCB 4 may for example be L-shaped for placing each UVC emitter at a desired height, see FIGS. 1A and 1B.

A distance between each of the first 5 and second 6 UVC emitters and a respective portion 15, 16 of the conduit may in some examples be less than 1 cm, and in particular less than 0.8 cm. Such a distance may in some examples be more than 0.2 cm.

A distance between a UVC emitter 5, 6 and a corresponding channel portion 15, 16 may be large enough for illuminating all the channel 14 with the two UVC emitters 5, 6 and may simultaneously be small enough for reducing a period of time during which the UVC emitters illuminate the channel. If the distance between a UVC emitter 5, 6 and the corresponding channel portion 15, 16 is too small, part of the channel may remain unirradiated. If the distance is too large, a longer period of time for disinfection may be required, and a service life of the UVC emitter may therefore be shortened. This distance may be measured along a reference axis or centre of irradiation. A reference axis or center of irradiation may be understood as a direction in which UVC light would be irradiated towards the channel if the UVC light was collimated. If UVC light is not collimated, the UVC light is emitted with an angular dispersion around the reference axis. In the example of FIG. 2, the reference axis 24 for each UVC emitter is illustrated.

The first 5 and second 6 UVC emitters may be light emitting diodes, LEDs. UVC LEDs may be small, have a long service life, and be resistant to impacts and high temperatures. They may therefore be suitable UVC emitters for a nebulizer device 10, especially for a portable nebulizer device, e.g. for treating the respiratory system. An opening angle of a UVC emitter, e.g. of a LED UVC emitter, may be between 110° and 150° in some examples. An opening angle may be measured from the reference axis or center, which could be the point where the UVC emitter emits its maximum light output, to the point where the UVC emitter emits 50% of its light output.

The channel 14, i.e. both the input 15 and outlet 16 portions of the channel, may comprise, e.g. be made of, optical silicone rubber. The optical silicone rubber may have a Shore A hardness between 10 and 50. The Shore A hardness for LSR may be determined by the method described in ISO 48-4:2018.

Optical silicone rubber may also be known as optical liquid silicone rubber, LSR. Optical silicone rubber is transparent for UV radiation, and this transparency does not tend to fade with time or with exposure to the UV radiation or to heat. Optical silicone rubber is lighter than glass and a lot of plastics, and it is also more flexible than glass. Silicone is furthermore biocompatible. Optical LSR may be optically and mechanically stable up to temperatures of 150° C. Therefore, a channel 14 comprising optical LSR, e.g. made of optical LSR, may be more durable in general than channels 14 not including this material. A hardness in the above range in the Shore A scale may provide sufficient rigidity to the channel 14 to guide the liquid composition as well as sufficiently flexibility to allow vibration of the mesh.

In some examples, the channel 14 may comprise, e.g. be made of, a thermoplastic elastomer. The thermoplastic elastomer may have a hardness between 10 and 50 in the Shore A scale. The hardness for a thermoplastic elastomer in the Shore A scale may be determined by the method described in ISO 823:2003. Thermoplastic elastomers, TPEs, may be sometimes referred to as thermoplastic rubbers, and are materials that have both thermoplastic and elastomeric properties. TPEs may be corrosion resistant, UV resistant and impact resistance. In combination with the optical LSR they may help to extend the service life of the channel 14. A TPE that may be used is a cyclic olefin copolymer (COC) elastomer, such as TOPAS® Elastomer E-140, commercially available from TOPAS Advanced Polymers.

Still in some other examples, the channel 14 may be made of a material that is substantially opaque to UV light, in particular to UVC light, and the channel 14 may include one or more quartz windows integrated in the wall of the opaque channel. For example, a quartz window may be positioned such that the light emitted by the UVC emitters is able to pass through the quartz windows and irradiate the channel 14.

The nebulizer device 10 may further comprise a signal emitter (not shown) in some examples for notifying a user when disinfection has ended. The signal emitter may provide a visual signal and/or a noise signal. For example, the user may see that a light switches on or off when disinfection has finished, or that a light changes color. Additionally or alternatively, a particular noise may be emitted, or a noise may stop, or a noise may change to indicate that disinfection is over.

The nebulizer device 10 may comprise a receptacle 2 for receiving a capsule 23, e.g. a disposable capsule. The capsule may contain the liquid composition and may be introduced in the receptacle 2 of the nebulizer device 10 e.g. in a substantially vertical manner. The capsule may be shaped and dimensioned to substantially match the receptacle 2.

The nebulizer device 10 may comprise, in some examples, a cutting element 12 for perforating a bottom end of the capsule 23. The cutting element 12 may for instance be arranged at the beginning of the input portion 15 of the channel 14 and may extend into the receptacle 2 of the nebulizer device. When the cutting element 12 cuts, e.g. perforates, a bottom of the capsule 23, the liquid composition may flow to the channel 14 and towards the mesh 11. Gravity may cause the liquid composition to flow towards the mesh 11. The cutting element 12 may be hollow in some examples and may comprise a substantially cylindrical portion. The cutting element 12 may be made of stainless steel.

The first 5 and second 6 UVC emitters may be arranged such that the cutting element 12 is illuminated at least by one of them when the UVC emitters are activated. The cutting element 12 may thus be disinfected at the same time as the channel 14, thereby enhancing disinfection of the nebulizer device 10. If the cutting element 12 is made of a stainless steel or comprises a specular surface, reflection of UVC radiation inside the cutting element may further increase the efficiency of disinfecting because more UVC radiation will reach surfaces and portions from which germs and bacteria need to be exterminated. In some examples, the UVC emitters 5, 6 may be facing the cutting element 12, the channel 14 being between the cutting element 12 and the UVC emitters 5, 6, see FIG. 1A.

The nebulizer device 10 may also comprise a start button to initiate the nebulization. The start button may be located in the casing 18, e.g. above or below a UVC emitter button 3. The start button may be linked with a mechanical switch or an electronic switch configured to initiate the nebulization. When a user or patient so indicates, a piezoelectric mesh actuator 9 arranged with the mesh 11, e.g. surrounding the mesh, may vibrate the mesh with a predetermined frequency during a predetermined time.

FIG. 3 is a flow diagram of an example of a method 30 for disinfecting a channel 14 of a nebulizer device 10 as disclosed herein. The method comprises, at block 31, initiating the channel 14 disinfection. For example, a button 3 provided in the casing 18 of the nebulizer device 10 may be pushed. Alternatively, charging a battery of the nebulizer device 10 may initiate the channel 14 disinfection. The method further comprises, at block 32 illuminating an input portion 15 of the channel 14 with UVC radiation from a first UVC emitter 5 arranged at a first side of a nebulizer mesh 11, and illuminating an output portion 16 of the channel 14 with UVC radiation from a second UVC emitter 5 arranged at a second opposite side of the nebulizer mesh 11. The method further comprises, at block 33, ending the channel 14 disinfection.

The illumination of the input 15 and output 16 portions of the channel 14 may be substantially simultaneous. I.e., illumination of both channel portions may start at a same time, and it may also end at a same time. This may allow for a faster disinfection of the channel 14. In other examples, UVC illumination may be partially overlapping or non-overlapping. For instance, disinfection of the input channel portion 15 and the output channel portion 16 may start substantially at a same time, but one of them may finish earlier than the other. Or disinfection of one of the channel portions 15, 16 may start and end, and disinfection of the other channel portion may start afterwards. The nebulizer device 10 may comprise a memory comprising instructions readable by a processor, and a processor configured to read the instructions stored in the memory and to execute them to indicate when UVC illumination starts and/or ends for one or both UVC emitters.

The input channel portion 15 and the output channel portion 16 may be illuminated between 5 and 15 minutes in some examples, e.g. between 5 and 9 minutes. Such a time range may provide an effective disinfection of the channel 14 in a fast manner.

Figure 3:
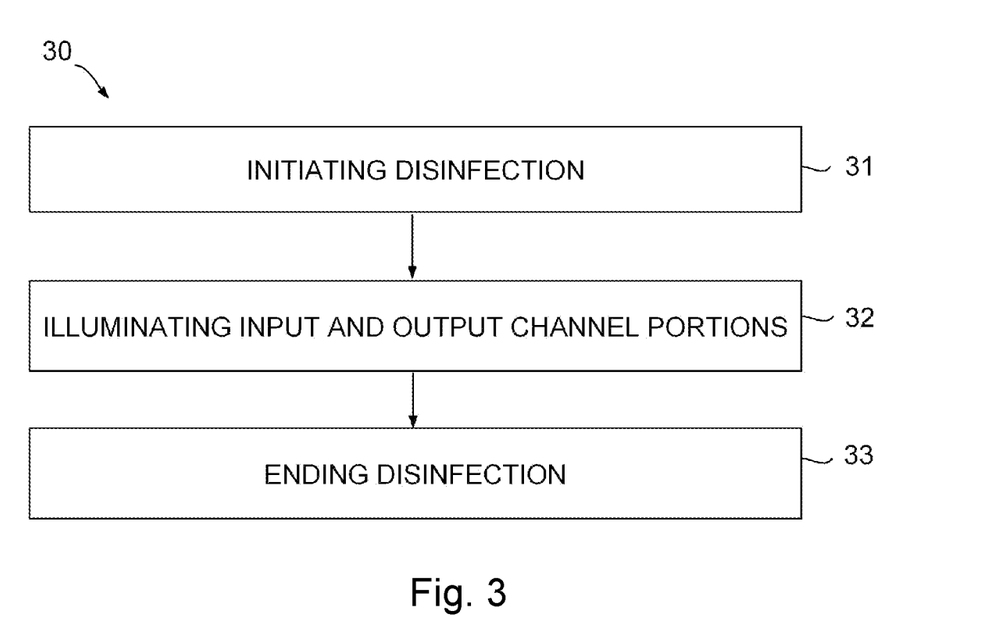
FIG. 3 is a flow diagram of a method for disinfecting the internal channel of a nebulizer device.

Ending 33 the channel disinfection may be manual in some examples. A user may, after a certain period of time, activate the UVC emitter actuator 3 for stopping disinfection. In other examples, the channel disinfection may be ended automatically. The nebulizer device 10 may be configured to stop the disinfection after a predetermined period of time, e.g. about 7 minutes. Automatic ending of the disinfection may be more convenient for a user, who would not need to worry about the time elapsed since e.g. pushing a UVC emitter button 3 or starting to charge a battery of the nebulizer device 10. Disinfection may be fast and complete each time.

This method 30 may be performed after a liquid composition has been nebulized in some examples. For instance, it may be performed after each nebulization of the liquid component. This may help to limit bacterial growth and to keep a clean and disinfected channel 14. In other examples, it may be performed before a liquid composition is nebulized, e.g. between 5 and 15 minutes before starting nebulization by pushing the start button of the nebulizer device 10.

As already mentioned, disinfection may be carried out during charging of the nebulizer device. The nebulizer device may include one or more rechargeable batteries for powering the vibration of the mesh and for disinfecting. After a user has performed a treatment, the nebulizer device may be connected to a power supply to recharge the batteries. The recharging does not necessarily have to be performed after each use but may instead be carried out at the end of a day or after a number of treatments, e.g. three nebulizing sessions. The nebulizer device may be programmed to start disinfecting when connected to a power supply.

For completeness, various aspects of the present disclosure will be set out in the following numbered clauses:

Clause 1. A device for nebulizing a liquid composition comprising:
a channel connecting a liquid composition inlet for receiving a liquid composition, a mesh configured to be vibrated by a mesh actuator for nebulizing the liquid composition, and a liquid composition outlet for expelling a nebulized liquid composition;
wherein the mesh divides the channel in an input portion of the channel and an output portion of the channel, the channel being at least partially optically transparent to disinfecting electromagnetic radiation;
a first emitter arranged at a first side of the mesh configured to illuminate the input portion of the channel with disinfecting electromagnetic radiation and a second emitter arranged at a second opposite side of the mesh configured to illuminate the output portion of the channel with disinfecting electromagnetic radiation.

Clause 2. The device of clause 1, wherein the first and second emitters are attached to a same printed circuit board, PCB 4.

Clause 3. The device of clause 2, wherein the PCB 4 is a PCB dedicated to the emitters.

Clause 4. The device of any of clauses 1-3, wherein the nebulizer device is powered by a rechargeable battery and includes electronic circuitry that is configured to activate the first emitter and the second emitter during charging of the rechargeable battery.

Clause 5. The device of any of clauses 1-4, wherein a distance between the first emitter and the input portion of the channel, and a distance between the second emitter and the output portion of the channel, is less than 1 cm.

Clause 6. The device of any of clauses 1-5, wherein the first and second emitters are arranged at different heights with respect to a bottom cover of the nebulizer device.

Clause 7. The device of any of clauses 1-6, wherein the first and second emitters are UVC emitters, and optionally wherein the UVC emitters are light emitting diodes.

Clause 8. The device of any of clauses 1-7, wherein an opening angle of the first and second emitters is between 110 and 150°.

Clause 9. The device of any of clauses 1-8, wherein the channel is at least partially made, and preferably completely made of optical silicone rubber having a hardness between 10 and 50 in the Shore A scale.

Clause 10. The device of any of clauses 1-9, wherein the channel is a channel that is opaque to UV radiation and the channel further comprises one or more quartz windows incorporated in a wall of the channel to allow UV radiation to reach an inside of the channel.

Clause 11. A method for disinfecting the channel 14 of the nebulizer device according to any of clauses 1-10, the method comprising:
initiating the channel disinfection;
illuminating the input portion of the channel with electromagnetic radiation from the first emitter, and illuminating an output portion of the channel with electromagnetic radiation from the second emitter; and
ending the channel disinfection.

Clause 12. The method of clause 11, wherein the input portion and output portion of the channel 14 are illuminated substantially simultaneously.

Clause 13. The method of clause 11 or clause 12, wherein the input portion 15 and the output portion 16 are illuminated between 3 and 10 minutes, and in particular between 5 and 9 minutes Clause 14. The method of any of clauses 11-13, wherein upon a completion of a disinfecting process the first UVC emitter and the second UVC emitter are automatically deactivated.

Clause 15. The method of any of clauses 11-14, wherein charging a battery of the nebulizer device 10 initiates the channel disinfection.

Clause 16. The method of any of clauses 11-15, wherein the first and second emitters emit bacterial disinfecting electromagnetic radiation.

Clause 17. The method of any of clauses 11-15, wherein the first and second emitters emit UVC radiation.

Clause 18. The method of any of clauses 11-17, wherein the first and second emitters emit blue light, specifically blue light with a wavelength in the range of 380-495 nanometers.

This written description uses examples to disclose the present teaching, including the preferred embodiments, and also to enable any person skilled in the art to practice it, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, can be mixed and matched by one of ordinary skill in the art to construct additional embodiments and techniques in accordance with principles of this application. If reference signs related to drawings are placed in parentheses in a claim, they are solely for attempting to increase the intelligibility of the claim, and shall not be construed as limiting the scope of the claim.

What is claimed is:

1. A nebulizer device for nebulizing a liquid composition, the nebulizing device comprising:

a channel connecting a liquid composition inlet for receiving a liquid composition, a mesh configured to be vibrated by a mesh actuator for nebulizing the liquid composition, and a liquid composition outlet for expelling a nebulized liquid composition;

wherein the mesh divides the channel into an input portion of the channel and into an output portion of the channel, the channel being defined at least in part by a first material that is at least partially optically transparent to disinfecting electromagnetic radiation; and first and second emitters that each is configured to emit disinfecting electromagnetic radiation, the first emitter arranged at a first side of the mesh and configured to illuminate the input portion of the channel with the disinfecting electromagnetic radiation, the second emitter arranged at a second side of the mesh opposite the first side and configured to illuminate the output portion of the channel with the disinfecting electromagnetic radiation;

the nebulizer device is powered by a rechargeable battery and includes electronic circuitry that is configured to activate the first and second emitters during a charging of the rechargeable battery.

2. The nebulizer device of claim 1, wherein the disinfecting electromagnetic radiation is UVC radiation.

3. The nebulizer device of claim 1, wherein the first and second emitters are attached to and electrically coupled to a same printed circuit board.

4. The nebulizer device of claim 3, wherein the printed circuit board is made of a metal having a thermal conductivity of 200 W/m·K or more.

5. The nebulizer device of claim 1, further comprising an actuator configured to activate the first and second emitters.

6. The nebulizer device of claim 1, wherein a distance between the first emitter and the input portion of the channel, and a distance between the second emitter and the output portion of the channel, is less than 1 cm.

7. The nebulizer device of claim 1, wherein the first and second emitters are arranged at different heights with respect to a bottom cover of the nebulizer device.

8. The nebulizer device of claim 1, wherein the first and second emitters are light emitting diodes.

9. The nebulizer device of claim 1, wherein an opening angle of the first and second emitters is between 110 and 150°.

10. The nebulizer device of claim 1, wherein the first material is an optical silicone rubber.

11. The nebulizer device of claim 10, wherein the optical silicone rubber has a hardness between 10 and 50 in the Shore A scale.

12. The nebulizer device of claim 1, wherein the first material comprises quartz.

13. The nebulizer device of claim 1, further comprising a cutting element that is configured to perforate a bottom end of a capsule to be received by the nebulizer device, wherein the first and second emitters are arranged such that the cutting element is illuminated by at least one of the first and second emitters when the at least one of the first and second emitters is activated.

14. A method for disinfecting the channel of a nebulizer device for nebulizing a liquid composition, the nebulizer device comprising:

a channel connecting a liquid composition inlet for receiving a liquid composition, a mesh configured to be vibrated by a mesh actuator for nebulizing the liquid composition, and a liquid composition outlet for expelling a nebulized liquid composition;

wherein the mesh divides the channel into an input portion of the channel and into an output portion of the channel, the channel being defined at least in part by a first material that is at least partially optically transparent to disinfecting electromagnetic radiation; and first and second emitters that each is configured to emit disinfecting electromagnetic radiation, the first emitter arranged at a first side of the mesh and configured to illuminate the input portion of the channel with the disinfecting electromagnetic radiation, the second emitter arranged at a second side of the mesh opposite the first side and configured to illuminate the output portion of the channel with the disinfecting electromagnetic radiation;

and the method comprising:

illuminating the input portion of the channel with the disinfecting electromagnetic radiation from the first emitter, and illuminating an output portion of the channel with the disinfecting electromagnetic radiation from the second emitter, wherein charging a battery of the nebulizer device triggers the illuminating by the first and second emitters.

* * * * *